US006428529B1

(12) United States Patent
Gruber et al.

(10) Patent No.: US 6,428,529 B1
(45) Date of Patent: *Aug. 6, 2002

(54) EPIDURAL ADMINISTRATION OF THERAPEUTIC COMPOUNDS WITH SUSTAINED RATE OF RELEASE

(75) Inventors: Andres Gruber; Sharad B. Murdande; Taehee Kim, all of San Diego; Sinil Kim, Solana Beach, all of CA (US)

(73) Assignee: SkyePharma Inc., San Diego, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/931,867

(22) Filed: Sep. 16, 1997

Related U.S. Application Data

(63) Continuation of application No. 08/502,569, filed on Jul. 14, 1995.

(51) Int. Cl.[7] ............................................. A61M 31/00
(52) U.S. Cl. ........................ 604/512; 604/500; 424/450; 424/457
(58) Field of Search ............................... 604/28, 49, 51, 604/890.1, 891.1, 892.1, 265; 424/450–457, 489–502; 128/898

(56) References Cited

U.S. PATENT DOCUMENTS

| 4,078,052 A | 3/1978 | Papahadjopoulous |
| 4,089,801 A | 5/1978 | Schneider |
| 4,145,410 A | 3/1979 | Sears |
| 4,224,179 A | 9/1980 | Schneider |
| 4,235,871 A | 11/1980 | Papahadjopoulous et al. |
| 4,310,506 A | 1/1982 | Baldeschwieler et al. |
| 4,394,372 A | 7/1983 | Taylor |
| 4,522,803 A | 6/1985 | Lenk et al. |

(List continued on next page.)

FOREIGN PATENT DOCUMENTS

| EP | 0 280 503 | 8/1988 | |
| GB | 2050287 | 1/1981 | |
| RU | 2100030 | 4/1990 | ............ A61K/9/10 |
| RU | 2103994 | 7/1991 | ............ A61K/9/52 |

(List continued on next page.)

OTHER PUBLICATIONS

Sinil Kim et al., "Multivesicular Liposomes Containing Cytarabine for Slow–Release Sc Administration," Cancer Treatment Reports, vol. 71, No. 5, pp. 447–450, May 1987.
Sinil Kim et al., "Direct Cerebrospinal Fluid Delivery of an Antiretorviral Agent Using Multivesicular Liposomes," Journal of Infectious Diseases, vol. 162, pp. 750–752, Sep. 1990.
Sinil Kim et al., "Multivesicular Liposomes containing 1–β–D–Arabinofuranosylcytosine for Slow–Release Intrathecal Therapy," Cancer Research, vol. 47, pp. 3935–3937, Aug. 1, 1987.
Huang, "Studies of Phosphatidylcholine Vesicles Formation and Physical Characteristics," Biochemistry, 8:334–352, 1969.

*Primary Examiner*—Brian L. Casler
*Assistant Examiner*—Catherine Serke
(74) *Attorney, Agent, or Firm*—Fish & Richardson P.C.

(57) ABSTRACT

A drug delivery system provides sustained-release delivery of therapeutic biologically active compounds administered epidurally. In the preferred embodiment the biologically active compound is an opioid, which is encapsulated within the non-concentric internal aqueous chambers or bilayers of multivesicular liposomes. The opioid is released over an extended period of time when the liposomes are introduced epidurally as a single dose for sustained analgesia.

2 Claims, 5 Drawing Sheets

U.S. PATENT DOCUMENTS

| | | | |
|---|---|---|---|
| 4,588,578 A | | 5/1986 | Fountain et al. |
| 4,599,227 A | | 7/1986 | Dees et al. |
| 4,610,868 A | | 9/1986 | Fountain et al. |
| 4,752,425 A | | 6/1988 | Martin et al. |
| 4,769,250 A | | 9/1988 | Forssen |
| 4,781,871 A | | 11/1988 | West, III et al. |
| 4,788,055 A | | 11/1988 | Fischer et al. ................. 424/79 |
| 4,816,264 A | | 3/1989 | Phillips et al. ............... 424/468 |
| 4,828,836 A | | 5/1989 | Elger et al. .................. 424/419 |
| 4,834,965 A | | 5/1989 | Martani et al. .............. 424/488 |
| 4,834,985 A | | 5/1989 | Elger et al. ................. 424/488 |
| 4,920,016 A | | 4/1990 | Allen et al. |
| 4,921,853 A | | 5/1990 | LeBlanc |
| 4,996,047 A | | 2/1991 | Kelleher et al. ............... 424/79 |
| 5,000,959 A | | 3/1991 | Iga et al. |
| 5,021,200 A | | 6/1991 | Vanlerberghe et al. |
| 5,071,646 A | | 12/1991 | Malkowska et al. ........ 424/497 |
| 5,077,056 A | * | 12/1991 | Bally et al. |
| 5,091,187 A | * | 2/1992 | Haynes ....................... 424/450 |
| 5,091,188 A | * | 2/1992 | Haynes ....................... 424/450 |
| 5,133,974 A | | 7/1992 | Paradissis et al. .......... 424/480 |
| 5,204,112 A | * | 4/1993 | Hope et al. |
| 5,211,955 A | * | 5/1993 | Legros et al. |
| 5,227,165 A | * | 7/1993 | Domb et al. |
| 5,244,678 A | * | 9/1993 | Legros et al. |
| 5,246,707 A | * | 9/1993 | Haynes |
| 5,261,903 A | * | 11/1993 | Dhaliwal et al. |
| 5,321,012 A | * | 6/1994 | Mayer et al. |
| 5,451,408 A | * | 9/1995 | Mezei et al. |
| 5,459,127 A | * | 10/1995 | Felgner et al. .................. 514/7 |
| RE35,192 E | * | 3/1996 | Reese |
| 5,612,057 A | * | 3/1997 | Lanza et al. ................. 424/450 |
| 5,922,340 A | * | 7/1999 | Berde et al. ................. 424/426 |
| 5,993,850 A | * | 11/1999 | Sankaram et al. .......... 424/450 |
| 6,132,766 A | * | 10/2000 | Sankaram et al. |

FOREIGN PATENT DOCUMENTS

| | | | |
|---|---|---|---|
| RU | 2039043 | 6/1992 | ......... A61K/31/445 |
| WO | WO 89/10125 | 11/1989 | |
| WO | WO 93/13128 | 7/1993 | |
| WO | WO 95/13796 | 5/1995 | |
| WO | WO 97/01351 | 1/1997 | |

OTHER PUBLICATIONS

Bangham, "Diffusion of Univalant Ions Across The Lamellae of Swollen Phospholipids," *J. Mol. Bio.,* 13:238–252, 1965.

Szoka, et al., Comparative Properties and Methods of Preparation of Lipid Vesicles (Liposomes), *Ann. Rev. Biophys. Bioengineering,* 9:467–508, 1980.

Shakiba, et al., "Evaluation of Retinal Toxicity and Liposome Encapsulation of the Anti–CMV Drug 2'–nor–cyclic CMP," *Investigative Opthalmology and Visual Science,* No. 10, 34:2903–2910, Sep. 1993.*

Frucht–Perry, et al., "Fibrin–Enmeshed Tobramycin Liposomes: Single Application Topical Therapy of . . . ," *Cornea,* No. 5, 11:393–397, Sep. 1992.*

Assil, et al., "Tobramycin Liposomes. Single Subconjunctival Therapy of . . . ," *Investigative Opthalmology and Visual Science,* No. 13, 32:3216–3220, Dec. 1991.*

Assil, et al., "Liposome Suppression of Proliferatative Vitreoretinopathy. Rabbit . . . ," *Investigative Opthalmology and Visual Science,* No. 13, 32:2891–2897, Oct. 1991.*

Turski, et al., "Magnetic Resonance Imaging of Rabbit Brain After Intracarotid Injection . . . ," *Magnetic Resonance in Medicine,* No. 2, 7:184–196, Jun. 1998.*

Skuta, et al., "Filtering Surgery in Owl Monkeys Treated With the Antimetabolite . . . ," *American Journal of Opthalmology,* No. 5, 103:714–716, May 15, 1987.*

Assil, et al., "Multivascular Liposomes. Sustained Release of the Anitmetabolite . . . ," *Archives of Opthalmology,* No. 3, 105:400–403, Mar., 1987.

Barbet, et al., "Weak Acid–Induced Release of Liposome–Encapsulated Carboxyfluorescein," *Biochimica et Biophysica Acta,* No. 3, 772:347–356, May 30, 1984.

Kim, et al., "Preparation of Cell–Size Unilamellar Liposomes with High Captured Volume and Defined Size . . . ," *Biochim. Biophys. Acta,* 646:1–9, 1981.

Kim, et al., "Preparation of Multivescular Liposomes," *Biochim. Biophys. Acta,* 728: 339–348, 1983.

Kim, et al., "Preparation of Multilamellar Vesicles of Defined Size–Distribution by Solvent–Spherule . . .," *Biochim. Biophys. Acta,* 812: 793–801, 1985.

Kim, et al., "Multivesicular Liposomes Containing Cytarabine Entrapped in the Presence of . . . ," *Cancer Treat Rep.,* 71: 705–711, 1987.

Kim, et al., "Multivesicular Liposomes Containing Cytosine 1–β–D–Arabinofuranosylcytosine for Slow–Release Intrathecal Therapy," *Cancer Treat. Rep.,* 47: 3935–3937, 1987.

Kim, et al., "Multivesicular Liposomes Containing Cytosine for Slow Release . . . ," *Cancer Treat. Rep.,* 71: 447–450 1987.

Kim, et al., "Modulation of the Peritoneal Clearance of Liposomal Cytosine Arabinoside by . . . ," *Cancer Chemother. Pharmacology,* 19:307–310, 1987.

Roy, et al., "Multivesicular Liposomes Containing Blemomycin for Subcutaneous Administration," *Cancer Chemother. Pharmacology,* 28: 105–108, 1991.

Kim, et al., "Prolongation of Drug Exposurein Cerebrospinal Fluid by Encapsulation Into . . .," *Camcer Chemother. Pharmacology,* 55: 1596–1598, Apr. 1, 1993.

Kim, et al., "Driect Cerebrospinal Fluid Delivery of an Antiretroviral Agent Using . . . ," *Jrnl. of Infectious Diseases,* 162: 750–752, 1990.

Chamberlain, et al., "Treatment of Leptomeningeal Metastasis with Intraventricular Administration of . . . ," *Archives of Neurol.,* 50: 261–264, 1993.

Chatelut, et al., "A Slow–Release Methotrexate Formulation for Intrathecal Chemotherapy," *Cancer Chemother. Pharmacol.,* 32:179–182, 1993.

Russack, et al., "Quantitative Cerebrospinal–Fluid Cytology in Patients Receiving Intracavitary Chemotherapy," *Ann. Neurol.,* 34:108–112, 1993.

Kim, et al., "Extended Cerebrospinal–Fluid Cytarabine Exposure Folling Intrathecal Adminstration of DTC 101," *J. Clin. Oncol.,* 11:2186–2193, 1993.

Kim, "Liposomes as Carriers of Cancer Chemotherapy: A Review," *Drugs,* No. 4, 46:618–638, 1993.

Kim, et al., "Extended–Release Formulation of Morphine for Subcutaneous Administration," *Cancer Chemother. Pharmacol.,* 33:187–190, 1993.

Ishii, "Production and Size Control of Large Unilamellar Liposomes by Emulisfication," *Liposome Technology,* 1:111–121, 1993.

Cullis, et al., "Structural Properties and Functional Roles of Phospholipids In . . . ," *Phospholipids and Cellular Regulation,* 1:65–123, 1985.

Bonetti, et al., "An–Extended–Release Formulation of Methotrexate For Subcutaneous . . .," *Cancer Chemotherapy and Pharmacology,* In Press, 1994.

Grunor, et al., "Novel Multilayered Lipid Vesicles: Comparison of Physical Characteristics of Multilamellar Liposomes and Stable Plurilamellar Vesicles," *Biochemistry,* No. 12, 24:2833–2842, Jun. 4, 1985.

Mashimo, T. et al., "Prolongation of canine epidural anesthesia by liposome encapsulation of lidocaine," *American Chemical Society,* 117:97227 (Abstract Only).

Reig, F. et al., "Preparation and in vitro activity of liposome encapsulated opioids," *Medline Express,* 1985–1989 (Abstract Only).

During, Matthew J., "Biochemical and behavioral recovery in a rodent model of Parkinson's disease following stereotactic implantation of dopamine–containing liposomes," *American Chemical Society,* 116:91304 (Abstract Only).

Hostetler, Karl Y., "Liposomes for prolonging the bioavailability and shelf life of therapeutic peptides and proteins", *American Chemical Society,* 115:15638 (Abstract Only).

Legros, Franz et al., "Pharmaceutical compositions containing liposome–encapsulated local anesthetics or central analgesics", *American Chemical Society,* 109:216008 (Abstract Only).

Murat–I, et al., "Continuous epidural anaesthesia for major abdominal surgery in young children", *Medline Express* 1985–1989 (Abstract Only).

* cited by examiner

EPIDURAL ADMINISTRATION OF THERAPEUTIC COMPOUNDS WITH SUSTAINED RATE OF RELEASE

This is a continuation of application Ser. No. 08/502,569, filed Jul. 14, 1995; pending.

THE FIELD OF THE INVENTION

This invention relates to controlled release of therapeutic compounds from drug delivery systems. More particularly, this invention relates to epidural administration of therapeutic compounds with sustained rate of release from a liposome formulation. This invention further relates to method of epidural catheter placement in a living vertebrate.

BACKGROUND

Post-operative pain management is a serious issue for patients and physicians, especially in the recovery room, as the patient is waking up from the anesthesia. Too generous a dose of systemic opioid given in an attempt to control pain can potentially cause life-threatening respiratory depression. On the one hand, either too little or too late a dose of post-operative pain medication can result in the patient waking up in intolerable severe pain. In addition, it has been shown that poorly controlled post-operative pain following abdominal or thoracic surgery inhibits ventilatory movement of the chest wall abdomen, and diaphragm, (P. R. Bromage, *Textbook of Pain*, P. D. Wall, et al. (Eds.): Churchill Livingstone, 1989, pp 744–753) resulting in pulmonary atelectasis.

The existence of opioid receptors in the spinal cord was discovered in the 1970's. Following initial clinical efficacy reports in 1979 (M. Behar et al., *Lancet* 1:527–529, 1979), epidural opioid administration has become very popular for post-operative pain control (T. I. Ionescu et al., *Act. Anaesth. Belg.* 40:65–77, 1989; C. Jayr et al, *Anesthesiology* 78:666–676, 1993; S. Lurie, et al. *European Journal of Obstetrics and Gynecology and Reproductive Biology* 49:147–153, 1993). Epidural opioids have the advantage of achieving good local analgesia at the spinal level without the loss of locomotor or vasomotor control or decreased level of consciousness.

Injectable opioids are widely used epidurally in post-operative and post-partum settings. Post-operative and post-partum pain usually lasts several days, but injectable opioids have relatively short durations of action (W. G. Brose et al., *Pain* 45:11–15, 1991; R. H. Drost et al., *Arzneim-Forsch/Drug Res.* 38:1632–1634, 1988; G. K. Gourlay et al., *Pain* 31:297–305, 1987). Thus, either continuous infusion or repeated injections are required to maintain adequate pain control (J. W. Kwan, *Am. J. Hosp. Pharm.* 47 (Suppl 1):S18–23, 1990; J. S. Anulty, *International Anesthesiology Clinics* 28:17–24, 1990; R. S. Sinatra, *The Yale Journal of Biology and Medicine* 64:351–374, 1991. Continuous infusion or repetitive injections further necessitate placement of catheter systems with or without attached infusion pumps, all of which consume expensive physician and nursing time for care and maintenance. Furthermore, repeated bolus injections or continuous infusions can result in respiratory depression.

Late respiratory depression and apneic episodes are the side-effects of greatest concern in early studies (P. R. Bromage, *Anesthesia and Analgesia* 60:461–463, 1981; E. M. Camporesi, et al., *Anesthesia and Analgesia* 62:633–640, 1983; T. L. Yaksh, *Pain* 11:293–346, 1981). A recent prospective non-randomized study of epidural morphine in 1085 patients who have undergone thoracic, abdominal, or orthopedic surgeries estimated the rate of "respiratory depression" following epidural morphine to be 0.9% (R. Stenseth et al., *Acta Anaesthesiol. Scand.* 29:148–156, 1985). As a comparison, the incidence of "life-threatening respiratory depression" in 860 patients given systemic morphine (PO, IV, IM, SC) was 0.9% (R. R. Miller et al, *Drug Effects in Hospitalized Patients.* John Wiley & Sons, New York, 1976). Prospective, randomized studies comparing epidural opioid versus systemic opioids (IM or IV) in high risk patients have shown that postoperative pain control with epidural opioid results in superior analgesia with decreased incidence of post-operative complications (N. Rawal et al., *Anesth. Analg.* 63:583–592, 1984; M P. Yeager, et al. *Anesth.* 60: 729–736, 1987).

The sustained release of various therapeutic agents after incorporation into liposomes, such as multivesicular liposomes, has been well documented both in vitro and in animals for intrathecal, subcutaneous, and intraperitoneal routes of administration, as well as in human patients for the intrathecal route of administration (S. Kim et al., *J. Clin. Oncol.* 11:2186–2193, 1993; V. Russack et al., *Ann Neurol.* 34:108–112, 1993; and M. C. Chamberlain et al., *Arch. Neurol.* 50:261–264, 1993). However, sustained release of epidurally administered compounds has heretofore been unknown in the art.

Therefore, the need exists for new and better methods for administering opioids and other therapeutic compounds epidurally as a single dose so as to achieve a sustained release rate at therapeutically effective levels. The present invention addresses the limitations of the prior art by providing a sustained-release formulation of a therapeutic agent such as an opioid, that results in maximal analgesia immediately after a single epidural dose and provides gradually decreasing analgesia over the next several days.

DESCRIPTION OF THE DRAWINGS

FIG. 1 is a series of four graphs recording the analgesic effect in rats over time following a single epidural dose of liposome-encapsulated morphine sulfate (DTC401) (open circles) or free morphine sulfate (closed circles) The intensity of analgesia is expressed as "percent of maximum possible analgesia (%MPA)". Each data point represents the average and standard error of mean (SEM) from 5 or 6 animals.

FIG. 4 is a series of five graphs comparing the percent oxygen saturation of hemoglobin ($SpO_2$) in rats over time following single epidural doses of epidural DTC401 (open circles) or free morphine sulfate (closed circles). Each data point represents the average and standard error of mean (SEM) from 5 animals except for 50 µg dose group where n=3.

FIG. 6 shows two graphs comparing the pharmacokinetics in rats of cerebrospinal fluid and serum following 250 µg epidural administration of DTC401 (open circles) or free morphine sulfate (closed circles). Each data point represents average and standard error of mean (SEM) from 3 or 4 animals.

SUMMARY OF THE INVENTION

Figure 1A:
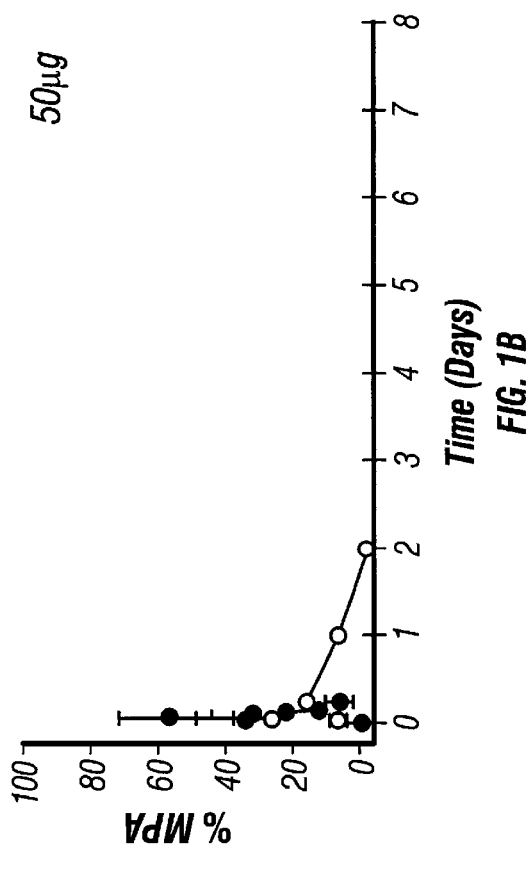
FIG. 1A shows the analgesic effect for a dosage of 10 $\mu$g.
Figure 1B:
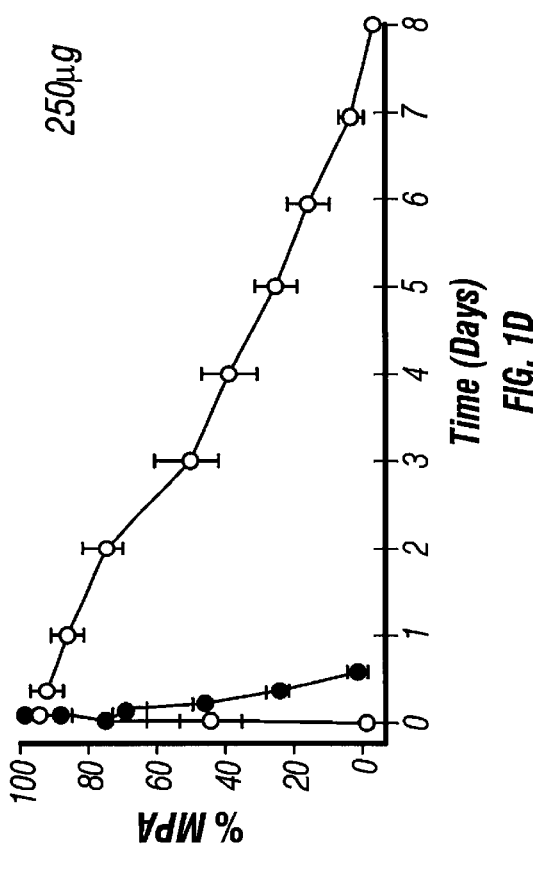
FIG. 1B shows the analgesic effect for a dosage of 50 $\mu$g.
Figure 1C:
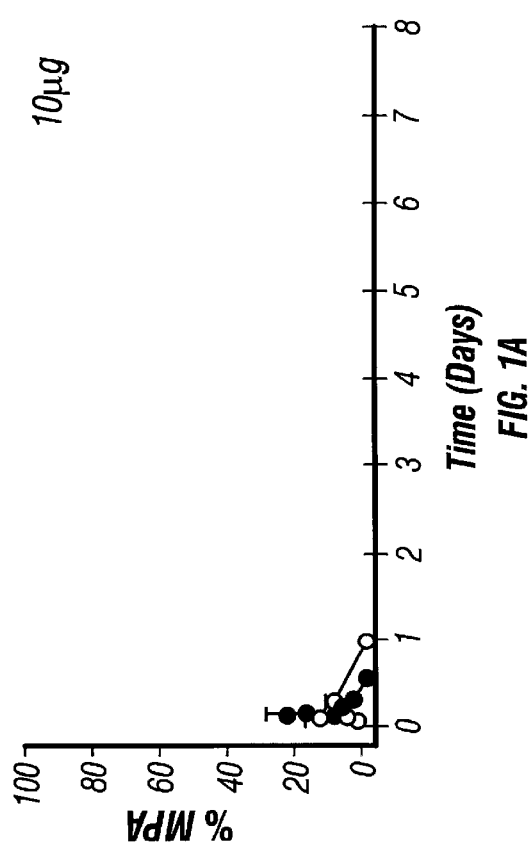
FIG. 1C shows the analgesic effect for a dosage of 175 $\mu$g.
Figure 1D:
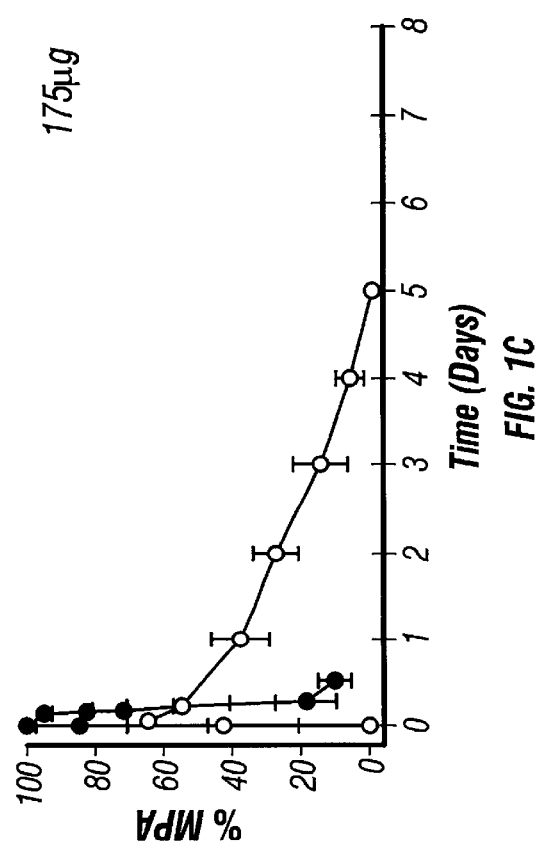
FIG. 1D shows the analgesic effect for a dosage of 250 $\mu$g.

Epidural administration of a therapeutic compound in a drug delivery system provided surprisingly greater sustained release and duration of therapeutic effect compared to use of free therapeutic compound.

Consequently, one aspect of the invention provides a method for the sustained release of a therapeutic compound by utilizing a drug delivery system administered epidurally to a vertebrate in need of such therapy.

Preferably, the vertebrate is a mammal such as a human. In various preferred embodiments, the drug delivery system is lipid based, especially when embodied as a multivesicular liposome.

The invention features the ability to allow sustained delivery of various therapeutic compounds, which, in preferred embodiments, encompass opioids or opiate antagonists, to allow modulation of analgesia. Alternate embodiments allow delivery of such therapeutic compounds as neurotrophic factors.

Furthermore, the use of a sustained-release formulation according to the method of the invention simplifies and reduces the over-all cost of epidural analgesia by eliminating the need for continuous infusion, multiple bolus injections, or emplacement of catheters, and also decreases the likelihood of infection. Even in the presence of epidural catheters, reduced frequency of injection is advantageous.

DETAILED DESCRIPTION OF THE INVENTION

The present invention presents a lipid-based sustained-release drug delivery system for epidural delivery of a therapeutic compound with epidural efficacy, such as an opioid. By epidural administration the compounds are released to the central nervous system and the cerebrospinal spinal fluid without puncturing the dura and at a sustained rate of release.

The term "sustained release" means that the therapeutic compound, when administered as a bolus dose encapsulated in the lipid-based formulation is released over a longer period of time as compared to epidural administration of the same drug in free form as a bolus injection. It does not necessarily mean that the concentration of the therapeutic compound remains constant for a sustained period of time. Generally, following surgery or post-partum, the patient experiences a decreasing amount of pain as the days pass. The patient's need for analgesia, therefore, also decreases over time. Using the method of epidural drug delivery of this invention, a therapeutically effective level of the therapeutic compound can be maintained in the cerebrospinal fluid and/or the serum over a period of several days, preferably from about 2 to about 7 days.

The term "therapeutic compound" as used herein means a chemical compound that has utility for modulating biological processes so as to achieve a desired effect in modulation or treatment of an undesired existing condition in a living being. The term therapeutic compound embraces chemical non-proteinaceous drugs, such as antibiotic and analgesics, as well as proteinaceous drugs, such as cytokines, interferons, growth factors, and the like.

Drug delivery systems are well known in the art. The present invention pertains to any sustained-release formulations such as synthetic or natural polymers in the form of macromolecular complexes, nanocapsules, microspheres, or beads, and lipid-based systems including oil-in-water emulsions, micelles, mixed micelles, synthetic membrane vesicles, and resealed erytirocytes. These systems are known collectively as dispersion systems. Dispersion systems are two-phase systems in which one phase is distributed as particles or droplets in a second phase. Typically, the particles comprising the system are about 20 nm–50 µm in diameter. The size of the particles allows them to be suspended in a pharmaceutical solution and introduced to the epidural space using a needle or catheter and a syringe.

Materials used in the preparation of dispersion systems are typically nontoxic and biodegradable. For example, collagen, albumin, ethyl cellulose, casein, gelatin, lecithin, phospholipids, and soybean oil can be used in this manner. Polymeric dispersion systems can be prepared by a process similar to coacervation or microencapsulation. If desired, the density of the dispersion system can be modified by altering the specific gravity to make the dispersion hyperbaric or hypobaric. For example, the dispersion material can be made more hyperbaric by the addition of iohexol, iodixanol, metrizamide, sucrose, trehalose, glucose, or other biocompatible molecules with high specific gravity.

One type of dispersion system which can be used according to the invention consists of a dispersion of the therapeutic agent in a polymer matrix. The therapeutic agent is released as the polymeric matrix, and decomposes or biodegrades into soluble products that are excreted from the body. Several classes of synthetic polymers, including polyesters (Pitt, et al. In *Controlled Release of Bioactive Materials*, R. Baker, Ed., Academic Press, New York, 1980); polyamides (Sidman, et al., *Journal of Membrane Science*, 7:227, 1979); polyurethanes (Master, et al., *Journal of Polymer Science, Polymer Symposium*, 66: 259, 1979); polyorthoesters (Heller, et al., *Polymer Engineering Science*, 21: 727, 1981); and polyanhydrides (Leong, et al., *Biomaterials*, 7: 364, 1986) have been studied for this purpose. Considerable research has been done on the polyesters of PLA and PLA/PGA. Undoubtedly, this is a consequence of convenience and safety considerations. These polymers are readily available, since they have been used as biodegradable sutures, and they decompose into non-toxic lactic and glycolic acids (see, U.S. Pat. Nos. 4,578,384; 4,785,973; incorporated by reference).

Solid polymeric dispersion systems can be synthesized using such polymerization methods as bulk polymerization, interfacial polymerization, solution polymerization, and ring opening polymerization (Odian, G., *Principles of Polymerization,* 2nd ed., John Wiley & Sons, New York, 1981). Using any of these methods, a variety of different synthetic polymers having a broad range of mechanical, chemnical, and biodegradable properties are obtained; the differences in properties and characteristics are controlled by varying the parameters of reaction temperatures, reactant concentrations, types of solvent, and reaction time. If desired, the solid polymeric dispersion system can be produced initially as a larger mass which is then ground, or otherwise processed, into particles small enough to maintain a dispersion in the appropriate physiologic buffer (see, for example, U.S. Pat. Nos. 4,452,025; 4,389,330; 4,696,258; incorporated by reference).

If desired, a therapeutic compound can be incorporated into a non-disperse structure which is epidurally implanted by surgical or mechanical means. A non-disperse structure is one having a defined overall shape, such as a slab, cylinder or sphere. The mechanism of release of therapeutic agent from biodegradable slabs, cylinders, and spheres has been described by Hopfenberg (in *Controlled Release Polymeric Formulations,* pp. 26–32, Paul, D. R and Harris, F. W., Eds., American Chemical Society, Washington, D.C., 1976). A simple expression describing additive release from these devices where release is controlled primarily by matrix degradation is:

$$M_t/M_\infty = 1 - [1 - k_o t/C_o \alpha]^n$$

where n=3 for a sphere, n=2 for a cylinder, and n=1 for a slab. The symbol α represents the radius of a sphere or cylinder or the half-thickness of a slab. $M_t$ and $M_\infty$ are the masses of drug released at time t and at infinity, respectively.

Any of the known lipid-based drug delivery systems can be used in the practice of the invention. For instance, multivesicular liposomes (MVL), multilamellar liposomes (also known as multilamellar vesicles or "MLV"), unilamellar liposomes, including small unilamellar liposomes (also known as unilamellar vesicles or "SUV") and large unilamellar liposomes (also known as large unilamellar vesicles or "LUV"), can all be used so long as a sustained release rate of the encapsulated therapeutic compound can be established. In the preferred embodiment, however, the lipid-based drug delivery system is a multivesicular liposome system. The method of making controlled release multivesicular liposome drug delivery systems is described in full in U.S. patent application Ser. No. 08/352,342 filed Dec. 7, 1994, now abandoned and Ser. No. 08/393,724 filed Feb. 23, 1995 now U.S. Pat. No. 5,576,017 and in PCT Application Serial Nos. US94/12957 and US94/04490, all of which are incorporated herein by reference in their entireties.

The composition of the synthetic membrane vesicle is usually a combination of phospholipids, usually in combination with steroids, especially cholesterol. Other phospholipids or other lipids may also be used.

Examples of lipids useful in synthetic membrane vesicle production include phosphatidylglycerols, phosphatidylcholines, phosphatidylserines, phosphatidylethanolamines, sphingolipids, cerebrosides, and gangliosides. Illustrative phospholipids include egg phosphatidylcholine, dipalmitoylphosphatidylcholine, distearoylphosphatidylcholine, dioleoylphosphatidylcholine, dipalmitoylphosphatidylglycerol, and dioleoylphosphatidylglycerol.

In preparing vesicles contairning a therapeutic agent, such variables as the efficiency of drug encapsulation, lability of the drug, homogeneity and size of the resulting population of vesicles, drug-to-lipid ratio, permeability, instability of the preparation, and pharmaceutical acceptability of the formulation should be considered. (Szoka, et al., *Annual Reviews of Biophysics and Bioengineering,* 9:467, 1980; Deamer, et al., in *Liposomes,* Marcel Dekker, New York, 1983, 27; Hope, et al., *Chem. Phys. Lipids,* 40: 89, 1986).

The use of lipid-based formulations of opioids has been investigated by others with limited success and none has been investigated via epidural route. For instance, preparation and in vitro activity of liposome encapsulated opioids has been studied (F. Reig, et al., *J. Microencapsulation* 6:277–283, 1989) without any epidural in vivo investigation. In addition, antinociception and side effects of alfentanil encapsulated in a liposome formulation and introduced by spinal delivery into rats has been explored (M. S. Wallace et al., *Anesth. Analg.* 79:778–786, 1994; C. M. Bernards et al., *Anesthesiology* 77:529–535, 1992). However, neither the pharmacokinetics nor the pharmacodynamics of these compounds were sufficiently different from those of the standard opioids to warrant their use in clinical practice. These studies did not explore sustained-release formulations of opioids given via the epidural route.

The lipid-based drug delivery system incorporating the therapeutic compound can be delivered as a single dose, for instance, via an epidural catheter. In the preferred embodiment, however, the lipid-based drug delivery system is injected as a single dose into the epidural space surrounding the spinal cord using a small gauge needle so that emplacement of a catheter is avoided. Preferably, an 18 gauge to 25 gauge needle is used.

A representative list of the therapeutic compounds useful for epidural delivery includes the opiates morphine, hydromorphone, codeine, hydrocodone, levorphanol, oxycodone, oxymorphone, diacetyl morphine, buprenorphine, nalbupine, butorphanol, pentazocine, methadone, fentanyl, sufentanyl and alfentanyl. In addition, opiate antagonists, such as naloxone and naltrexone, can be administered epidurally using the method of the invention to reverse or antagonize opiate effect.

Peptides and peptidomimetics that bind to one or more neuroreceptors such as the delta opioid, mu-opioid, kappa opioid and episilon-opioid receptors are considered opioids and can be administered for therapeutic effect according to the method of the invention. Such compounds include enkephalins, endorphins, casomorphin, kyotorphin, and their biologically active fragments. As used herein, the term "biologically active fragment" means any portion of a therapeutic compound that substantially retains the biological activity of the complete therapeutic molecule. One skilled in the art will know, or can easily determine, whether a fragment substantially retains the biological activity of the whole molecule.

In addition to opioids, a number of compounds having therapeutic utility when administered epidurally at a sustained rate can also be used in the practice of the method of the invention. These compounds include neurotrophic factors, such as insulin-like growth factor, ciliary neurotrophic factor and nerve growth factors; neurotransmitters and their antagonists, such as dopamine, epinephrine, norepinephrine, and gamma-amino butyric acid; local anesthetics, such as tetracaine, lidocaine, bupivacaine, and mepivacaine; substance P and related peptides; and alpha-2-receptor agonists, such as clonidine and dexmedetomidine. Further, co-administration of local anesthetics such as lidocaine, bupiracaine, and tetracaine can increase efficacy of epidural opioids.

In the present invention, it is shown that a lipid-based drug delivery system incorporating an opioid, such as morphine sulfate, has minimal potential for respiratory depression as measured by percent decrease in hemoglobin oxygen saturation ($SpO_2$) from the maximum blood oxygen saturation or baseline value prior to administration of the drug, compared to epidural administration of the free drug. One skilled in the art will appreciate that blood oxygen content can readily be measured by such commercially available devices as a pulse oximeter.

It is also shown that a single dose of sustained release opioid formulated in a multivesicular liposome composition and administered epidurally results in prolonged duration of analgesia, with the peak cisternal CSF concentration of the therapeutic drug occurring within 60 minutes after a single epidural dose and then gradually decreasing over the next several days, for instance up to eight days. Although the peak CSF concentration was decreased compared with that following epidural administration of free morphine sulfate, the total analgesia delivered (as shown, for example, by the area under the curve (AUC) in FIGS. 1, 3, and Table 1) was increased many fold compared to epidurally delivered free morphine sulfate. For instance, in rats there were 17- and 3.1-fold reductions in the peak serum and CSF morphine concentrations, respectively, but CSF AUC was increased 2.8 fold following epidural administration of 250 μg of morphine sulfate encapsulated in multivesicular liposomes (DTC401) compared to an identical dose of unencapsulated morphine sulfate.

Because of the reduction in the peak serum and CSF concentrations of morphine, there was no respiratory suppression with the controlled release of epidurally administered morphine; whereas epidurally administered free morphine did cause respiratory suppression at high dosages.

The chief advantages of the present invention are three-fold. First, the method of epidural delivery of a single dose of sustained release compound provides the advantage that the patient experiences a reduced risk of dose-related adverse effects, such as respiratory depression normally associated with bolus epidural injections or infusions of a therapeutic compound. Second, by administration of the therapeutic compound epidurally rather than directly into the cerebrospinal fluid, the therapeutic compound does not migrate all over the brain and spinal cord, and a therapeutically effective dosage of the therapeutic compound is released locally into the epidural space over an extended period of time, for instance up to eight days. And finally, prolonged analgesia is obtained without multiple injections or continuous infusions.

One skilled in the art will comprehend that the period of time over which a therapeutic rate of release is maintained in the practice of the invention will vary depending upon the disease state to be treated, the characteristics of the therapeutic compound and the sustained-release drug delivery system, and the total amount of the compound encapsulated and administered to the patient.

The term "therapeutically effective" as it pertains to the compositions of the invention means that the therapeutic compound is released from the drug delivery system at a concentration sufficient to achieve a particular medical effect for which the therapeutic agent is intended. For instance, if the therapeutic compound is an opioid, the desirable medical effect is analgesia without respiratory depression. Exact dosages will vary depending upon such factors as the particular therapeutic compound and desirable medical effect, as well as patient factors such as age, sex, general condition, and the like. Those of skill in the art can readily take these factors into account and use them to establish effective therapeutic concentrations without resort to undue experimentation.

For instance, the dosage range appropriate for epidural administration of morphine sulfate to a human includes the range of 1 mg to 60 mg. More potent compounds can require dosages as low as 0.01 mg and less potent compounds can require 5000 mg. While doses outside the foregoing dose range may be given, this range encompasses the breadth of use for practically all the therapeutic substances contemplated for administration by an epidural route.

Previously published methods of epidural placement in rats involves drilling a hole through a lumbar vertebral bone and pushing a catheter 1 cm up the epidural space. The present invention enables placement of a catheter from above (i.e., from the cervical region) without the trauma of a surgical procedure. Also, the catheter tip can be placed at any location along with the vertebral column rather than being restricted to the lumbar region as described in the prior art. This method of catheter placement from above is also applicable to animals other than rats, such as rabbits, dogs, and humans.

The following examples illustrate the manner in which the invention can be practiced. It is understood, however, that the examples are for the purpose of illustration and the invention is not to be regarded as limited to any of the specific materials or conditions therein.

EXAMPLE 1

A. Preparation of Multivesicular Liposomes Encapsulating Morphine Sulfate (DTC401) in the Presence of a Hydrochloride Step 1) In a clean one-dram glass vial (1.3 cm inner diameter×4.5 cm height), were placed 1 ml of a chloroform (Spectrum Corp., Gardena, Calif.) solution containing 9.3 μmoles of dioleoyl lecithin (Avanti Polar Lipids, Alabaster, Ala.), 2.1 μmoles of dipaimitoyl phosphatidylglycerol (Avanti Polar Lipids), 15 μmoles of cholesterol (Avanti Polar Lipids), and 1.8 μmoles of triolein (Sigma). This solution is referred to as the lipid component.

Step 2) One ml of an aqueous solution containing 20 mg/ml of morphine sulfate (Sigma Chemical Co., St. Louis, Mo.) and 0.1N of hydrochloric acid, was added into the above one-dram glass vial containing the lipid component.

Step 3) For making the water-in-oil emulsion, the glass vial containing the mixture of "Step 2" was sealed and attached horizontally to the head of a vortex shaker (Catalogue #S8223-1, American Scientific Products, McGaw Park, Ill.) and shaken at maximal speed for 6 minutes.

Step 4) For making the chloroform spherules suspended in water, the water-in-oil emulsion obtained from "Step 3" was divided in equal volume and expelled rapidly through a narrow-tip Pasteur pipette into each of two one-dram glass vials (1.3 cm inner diameter×4.5 cm height), each containing 2.5 ml water, glucose (32 mg/ml), and free-base lysine (40 mM) (Sigma). Each vial was then sealed, attached to the head of the same vortex shaker as used in "Step 3" and shaken for 3 seconds at maximal speed to form chloroform spherules.

Step 5) To obtain the multivesicular liposomes, chloroform spherule suspensions produced in the two vials of "Step 4" were poured into the bottom of a 250 ml Erlenmeyer flask containing 5 ml of water, glucose (32 mg/ml), and free base lysine (40 mM). With the flask kept at 37° C. in a shaking water bath, a stream of nitrogen gas at 7 L/minute was flushed through the flask to slowly evaporate chloroform over 10–15 minutes. The liposomes were then isolated by centrifugation at 600×g for 5 minutes; and washed three times in 0.9% NaCl solution.

B. Preparation of Formulations

Prior to epidural injection, preparations of the DTC401 and a control of unencapsulated ("free") morphine sulfate were adjusted so that 50 µl contained the dose of 10, 50, 175, 250 or 1000 µg. In addition, a preparation of MVLs containing a 2000 µg dose of morphine sulfate to be used in a study of respiratory suppression was formulated in a 75 µl volume for injection. The concentration of morphine in the various liposome formulations was determined by dissolving 50 µl of each preparation with 1 ml of isopropyl alcohol, followed by dilution in water. The morphine concentration was assayed with HPLC using a published method (S. P. Joel et al., *Journal of Chromatography* 430:394–399, 1988). For the placebo control, a blank multivesicular liposome composition was made by substituting glucose in place of morphine sulfate.

EXAMPLE 2

A. Animal Preparation

Six- to 8-week old male Sprague-Dawley rats weighing 205–254 g (Harlan Sprague-Dawley, San Diego, Calif.) were housed, 1 or 2 per cage, in a temperature-controlled environment with an alternating 12-hour light and darkness cycle and given unrestricted access to food and water. Prior to each study, animals were habituated to the environment. Each animal was studied only once. All animals were maintained in accordance with guidelines of the Committee on Care and Use of Laboratory Animals of the Institute of Laboratory Animal Resources, National Research Council.

B. Epidural Catheterization

Caudal epidural catheterization of rats was performed as follows: Halothane anesthesia was induced and the animals were placed in stereotaxic recumbency 7 cm in height. The head was flexed, taking care that animals maintained normal breathing. A short-beveled 19-gauge needle was inserted at an angle of approximately 170° to the spine just caudad to the occipital crest in the midline with needle bevel facing down. The needle was advanced caudad towards the C1 vertebra until the needle tip touched the spinous process or posterior lamina of C1. The needle tip was walked carefully to the ventral edge of the posterior lamina. At this point, a slight give was felt and the needle was advanced 1–2 mm further. Care was taken not to let the needle penetrate the dura. Accidental violation of the dura can be determined by a flash of cerebrospinal fluid (CSF) through the hub of the needle or through the subsequently-placed catheter.

A polyethylene catheter (PE-10; length: 12 cm, i.d.: 0.28 mm; volume: 7.4 µl (Becton Dickinson, Sparks, Md.) was threaded through the needle into the dorsal epidural space. The catheter was advanced slowly through the needle and stopped at the approximate level of L1, 8 cm from C1. The exposed portion of the catheter was subcutaneously tunneled under the scalp and fixed with a purse-string 3-0 silk suture. Finally, the catheter was flushed with 10 µl of normal saline and plugged with a stainless steel wire. The procedure from initiation of anesthesia to sutures lasted approximately 10 to 15 minutes. Animals were allowed to recover and were observed for a period of 60 minutes. Only those animals that completely recovered from the procedure were used in the following studies.

C. Antinociception

Baseline values of nociception following placement of the epidural catheter were determined by subjecting the animals to standard hot plate (52.5±0.5° C.) testing as described in M. S. Wallace et al., (*Anesth. Analg.* 79:778–786, 1994). Response latency to nociception (in seconds) was measured from the time when the animals were placed on the hot plate to the time when they either licked their hind paw or jumped. The baseline (pretreatment) response latency value was defined as 0% of the maximum possible analgesia (MPA) in each experimental animal. Then each animal was injected epidurally with 50 µl of either DTC401 containing doses of epidural morphine ranging from 10 µg to 250 µg, unencapsulated morphine sulfate solution, or control MVL blanks. The antinociceptive effect of subcutaneously administered morphine sulfate was also determined in a dose range of 250 µg to 1 mg. Following epidural administration of the test solutions via the catheter emplanted as described above, the epidural catheter was flushed with 10 µl of 0.9% sodium chloride.

The animals were then subjected to hot plate testing again for measurement of antinociceptive effect at specific time points: 0.5, 1, 2, 3, 4, 6, 12, and 24 hours following administration for unencapsulated morphine sulfate and 0.5, 1, 6 hours and 1, 2, 3, 4, 5, 6, 7, and 8 days following administration for both DTC401 and the MVL blanks. Antinociception was determined in 5 or 6 animals for each dose and each drug. To prevent tissue damage to the footpads, a cutoff time of 60 seconds was used. Accordingly, 100% MPA was defined as antinociception lasting ≧60 seconds. A latency interval of 10±2 to 60 seconds corresponding to an MPA of 0% to 100%, respectively. was sensitive for demonstrating dose-response in the studied dose range.

Efficacy and respiratory depression curves were plotted as a function of time for each dose administered. Hot plate responses were calculated as a percentage of the maximum possible analgesia (%MPA) as described in Wallace et al. (supra):

$$\% \ MPA = \frac{\text{Postdrug latency} - \text{Predrug latency}}{\text{Cutoff latency} - \text{Predrug latency}} \times 100\%$$

All areas under the curves were calculated by the trapezoidal rule to the last data point using the RSTRIP computer program [Micromath, Salt Lake City, Utah].

One-way analysis of variance (ANOVA) was used to separately determine dose dependency for the different drug formulations and routes; whereas two-way ANOVA was used for comparison between formulations at an equal dose. The Newman-Keuls test was performed on all ANOVA analyses to determine statistical significance; $p<0.05$ was considered statistically significant for all tests. All data is displayed as the mean±standard error of the mean (SEM).

Figure 2:
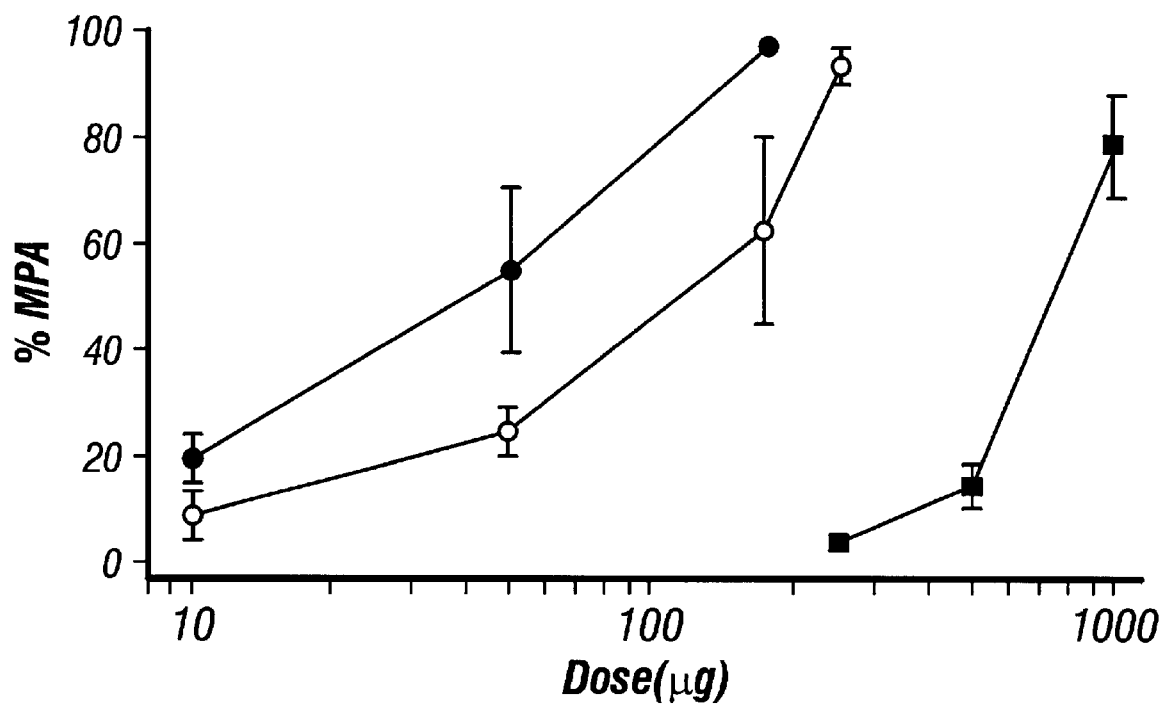
FIG. 2 is a graph showing the peak-analgesia dose-response curves as measured in rats after a single epidural dose of DTC401 (open circles), free morphine sulfate (close circles), or after a single subcutaneous dose of free morphine sulfate (closed squares). The average peak %MPA±SEM was obtained from 5 or 6 animals.

As shown by the data in FIG. 1, the epidural administration of DTC401 resulted in equivalent onset of analgesia, but the duration of analgesia was significantly prolonged compared to epidurally administered free morphine sulfate. Epidural injection of control MLV blanks showed no demonstrable antinociceptive effect (data not shown). The peak analgesic effects of epidural DTC401 and epidural and subcutaneous morphine sulfate were dose dependent, as shown in FIG. 2, with the peak-analgesia potency of epidural free morphine sulfate being greater than that of epidural DTC401, which is substantially greater than that of subcutaneously administered free morphine sulfate (p<0.05 for each comparison).

Figure 3:
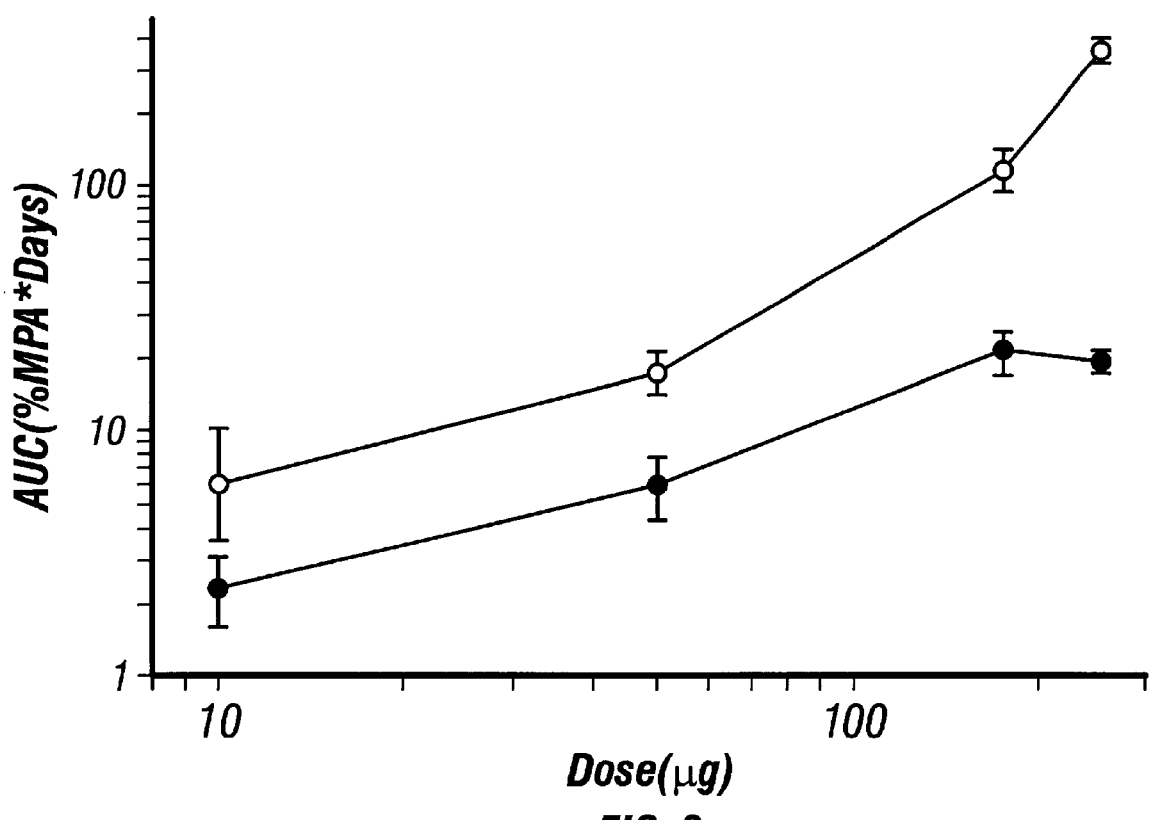
FIG. 3 is a graph comparing the total-analgesic effect in rats [as measured by the area under the analgesia-time curves (AUC)] for single doses of epidural DTC401 (open circles), or free morphine sulfate (closed circles). Each data point represents the average and standard error of mean (SEM) from 5 or 6 animals.
Figure 4A:
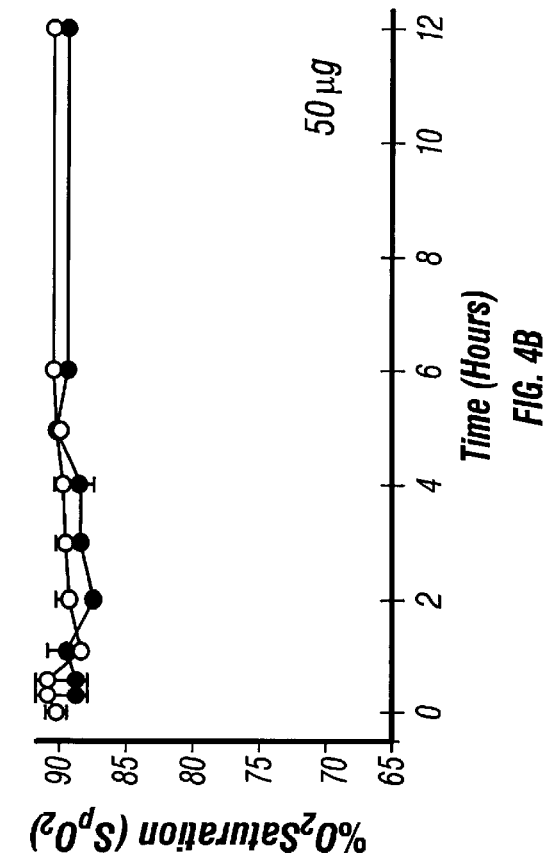
FIG. 4A shows the oxygen saturation for a dosage of 10 µg.
Figure 4B:
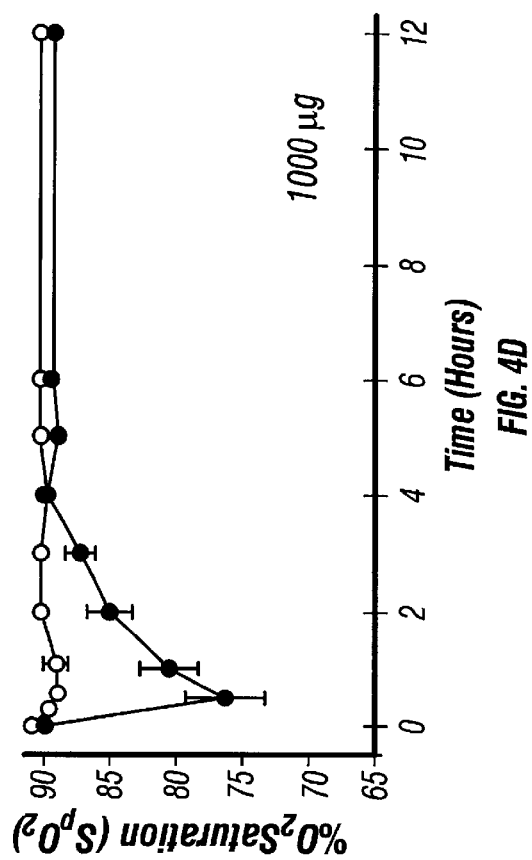
FIG. 4B shows the oxygen saturation for a dosage of 50 µg.
Figure 4C:
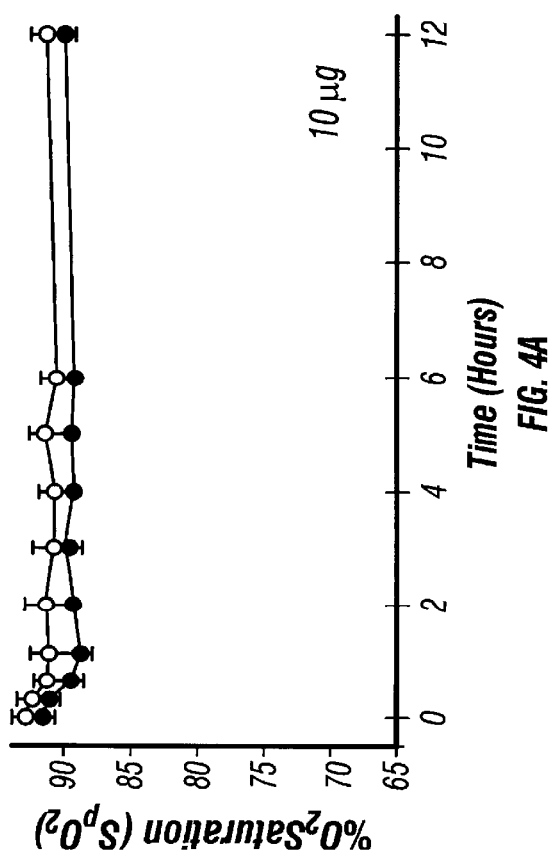
FIG. 4C shows the oxygen effect for a dosage of 175 µg.
Figure 4D:
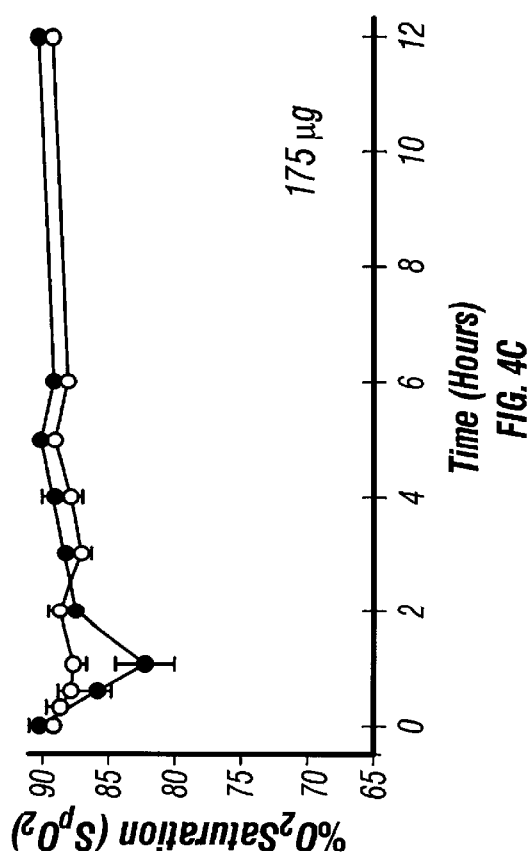
FIG. 4D shows the analgesic effect for a dosage of 1000 µg.
Figure 4E:
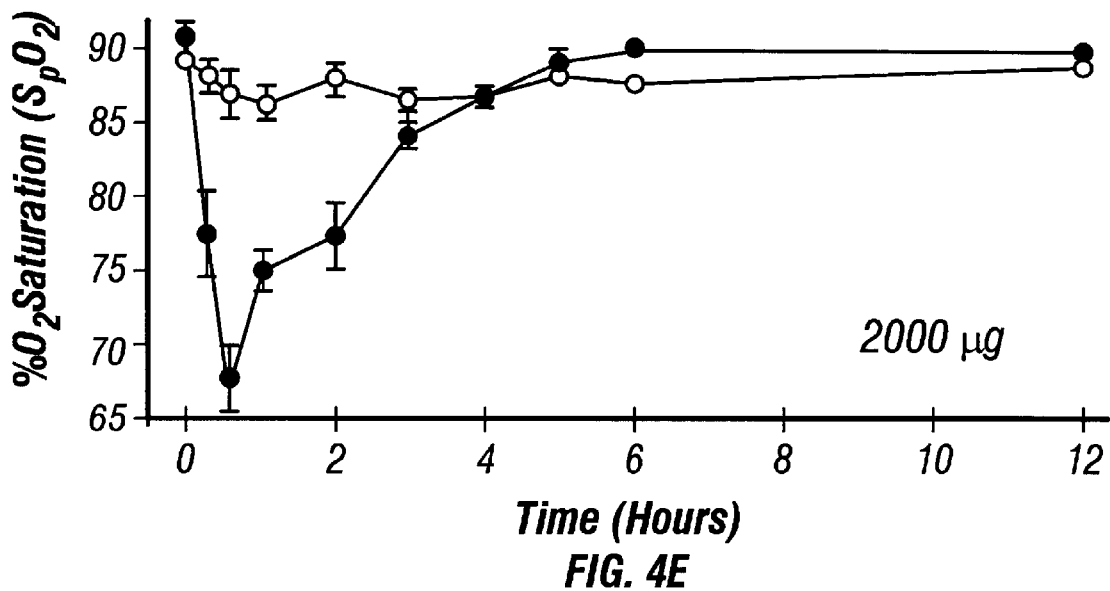
FIG. 4E shows the analgesic effect for a dosage of 2000 µg.

Substantial prolongation of analgesic effects in animals given epidural DTC401 is seen readily in FIG. 1 as well as by the large area-under-the-curve values (AUC) for DTC401 in FIG. 3. At the dose of 250 μg, which produced peak effects close to 100% MPA for both DTC 401 and free morphine sulfate, the time to decrease to 50% MPA was 3.4 days for DTC 401 compared to 0.17 day for morphine sulfate.

D. Respiratory Depression

Respiratory depression was quantified by pulse oximetry. The animals were removed from their cages, placed in polystyrene rat restraints (Plas Labs, Lansing, Mich.) and allowed to acclimate for 5 minutes. Oxygen saturation was determined at baseline and following a single epidural bolus of morphine sulfate or DTC401 at specific time points by placing a pulse oximeter probe on the right hind paw (Ohmeta Medical Systems, model 3740, Madison, Wis.). The doses of DTC401 and free morphine sulfate ranged from 10 to 2000 μg. Pulse oximetry was performed on 5 to 6 animals at each data point, except for the 50 μg dose where 3 animals were used. The pulse oximetry values of percent hemoglobin oxygen saturation ($SpO_2$) were monitored continuously in real time. The maximum value obtaining during the 3-minute recording period was defined as oxygen saturation.

Figure 5:
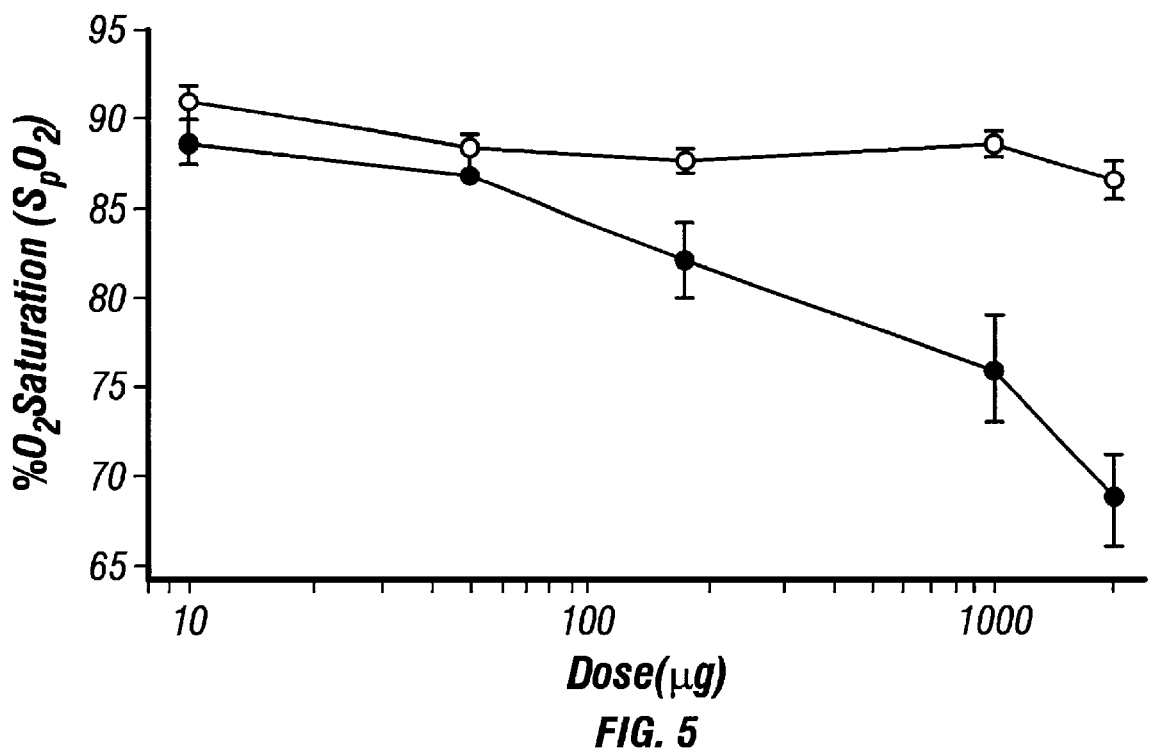
FIG. 5 is a graph showing the maximum respiratory-depression dose-response curve in rats after a single epidural dose of DTC401 (open circles) or free morphine sulfate (close circles). The lowest $SpO_2$ achieved was plotted against epidural morphine dose. Each data point represents the average and standard error of mean (SEM) from 5 animals except for 50 µg dose group where n=3.

FIG. 4 depicts the time course of percent oxygen saturation of hemoglobin ($SpO_2$) as measured by the pulse oximeter at various doses of DTC401 and morphine sulfate. There was a dose-dependent increase in respiratory depression with increasing doses of morphine sulfate as shown in FIG. 5; whereas minimal respiratory depression was produced by the same doses of DTC401. On the other hand, the maximum decreases in $SpO_2$ were observed within 1 hour following epidural administration of free morphine sulfate or DTC401, and no delayed respiratory depression was seen with either formulation. The difference between morphine sulfate and DTC401 on peak respiratory depression was statistically significant (p<0.01).

E. Pharmacokinetics

The pharmacokinetic studies were done by measuring morphine concentrations in peripheral blood and in CSF at appropriate time points following a single 250 μg epidural dose of DTC401 or free morphine sulfate. Samples were drawn at 0.5, 1 hours, and 1, 3, 5, 8 days following epidural administration as described above of DTC401 and at 0.5, 1, 3, 6, 12, 24 hours following epidural administration of free morphine sulfate. A set of 3 or 4 animals were anesthetized using halothane, and CSF and blood samples were collected via cisternal tap and cardiac puncture, respectively. The animals were then sacrificed by overdose of halothane. Serum was separated from blood by centrifugation and stored along with CSF samples at −80° C. until further analysis by radioimmunoassay (RIA).

Morphine concentrations in serum and CSF were determined using a commercially available RIA kit highly specific for morphine [Coat-A-Count™ Serum Morphine, Diagnostic Products Corp., Los Angeles, Calif.] as suggested by the manufacturer. All measurements were done in duplicate.

Figure 6A:
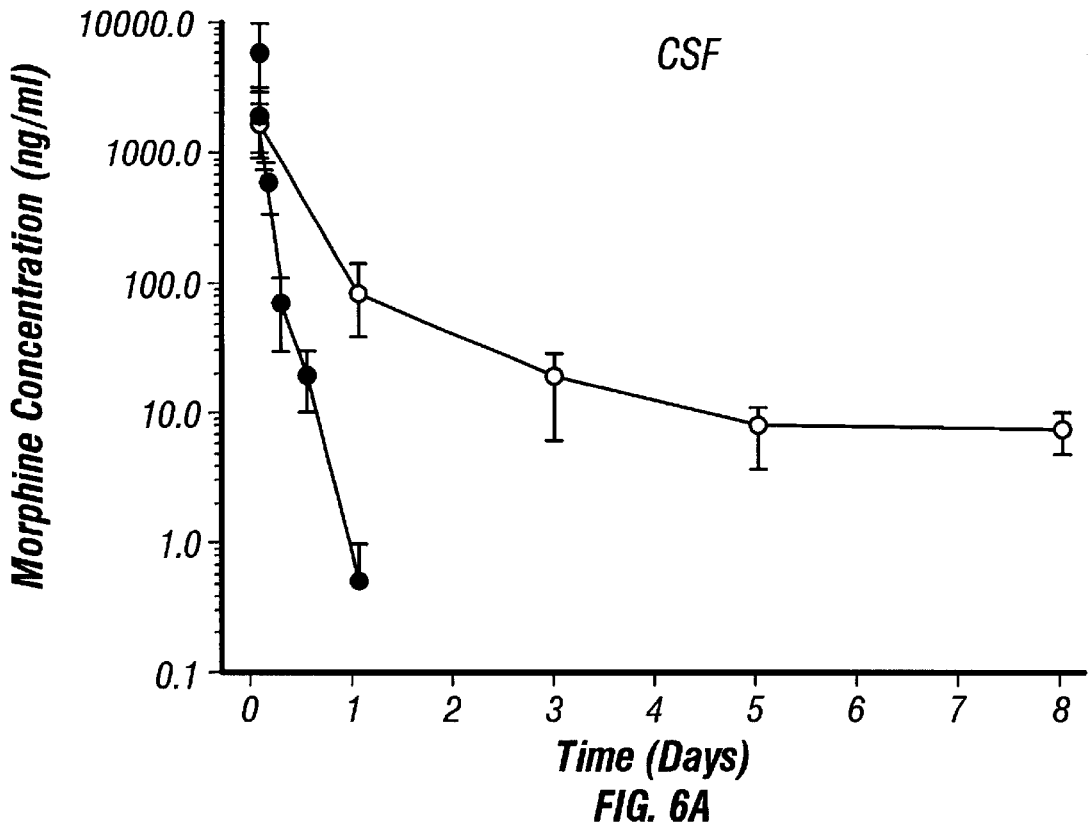
FIG. 6A shows the pharmacokinetics for cerebrospinal fluid.
Figure 6B:
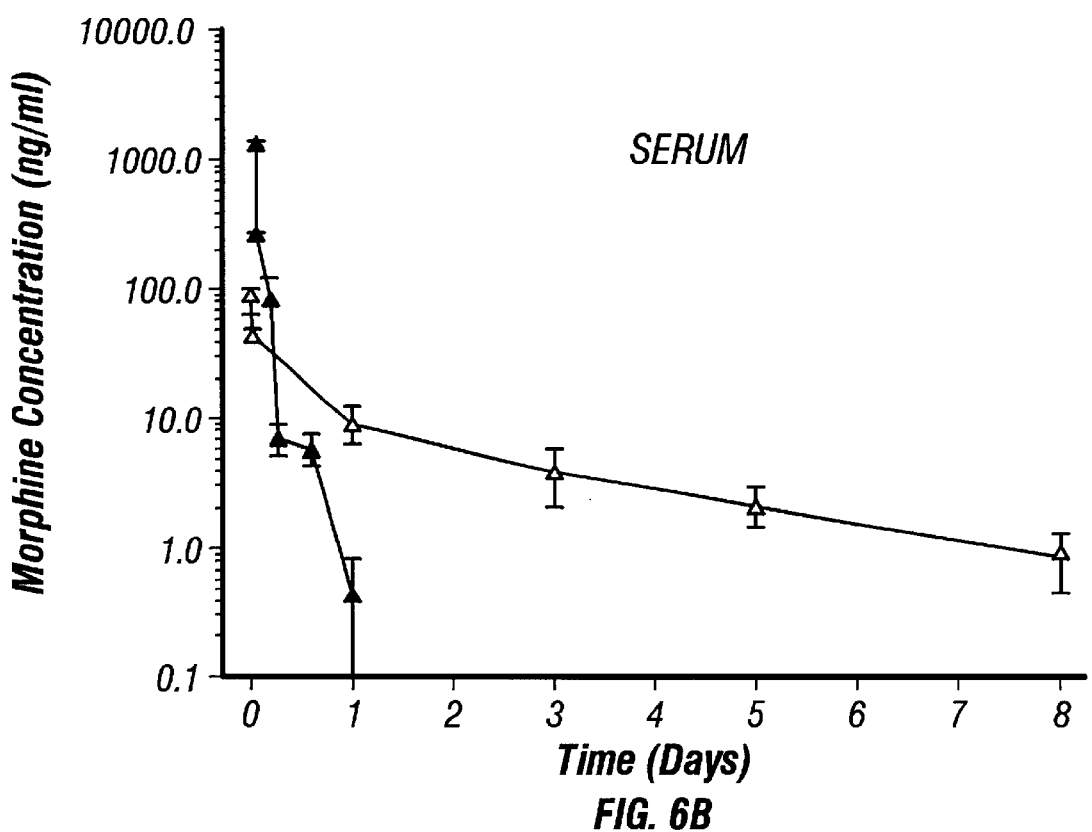
FIG. 6B shows the pharmacokinetics for serum.

FIG. 6 shows the concentrations of cisternal CSF and serum morphine in animals injected with 250 μg of free morphine sulfate or DTC401. Table 1 summarizes the pharmacokinetic parameters. The peak CSF and serum morphine concentrations following epidural administration of DTC401 were, respectively, 32% and 5.9% of that following morphine sulfate. The terminal CSF half-life (β) for DTC401 was 82 hours compared to 2.6 hours for morphine sulfate. The CSF area under the curve (AUC) was increased 2.7 times for DTC401 compared to morphine sulfate, but the plasma AUC was very similar. Half-lives were calculated by fitting the pharmacokinetic curves to a biexponential function. The RSTRIP program was used to perform the curve fitting by iterative nonlinear regression.

EXAMPLE 3

Larger Scale Preparation of DTC401

Step 1) Into a clean stainless steel 50 ml centrifuge tube were placed 5 ml of a chloroform solution containing 46.5 μmoles of dioleoyl phosphatidylcholine (Avanti Polar Lipids), 10.5 μmoles of dipaimitoyl phosphatidylgylcerol (Avanti Polar Lipids), 75 μmoles of cholesterol (Sigma Chemical Co.), 9.0 μmoles of triolein (Avanti Polar Lipids). This solution is referred to as the lipid component.

Step 2) Five ml of an aqueous solution containing 20 mg/ml of morphine sulfate pentahydrate (Mallinckrodt Chemical Inc.) and 0.1 N of hydrochloric acid was added into the above stainless steel centrifuge tube containing the lipid component.

Step 3) For making the water-in-oil emulsion, the mixture of Step 2 was stirred with a TK mixer (AutoHomoMixer, Model M, Tokushu Kika, Osaka, Japan) at a speed of 9000 revolution per minute (rpm) for 9 minutes.

Step 4) For making the chloroform spherules suspended in water, 25 ml of solution containing 4 percent glucose and 40 mM lysine in water was added to the water-in-oil emulsion of Step 3 and then mixed at a speed of 3500 rpm for 120 seconds.

Step 5) To obtain the multivesicular liposomes, the chloroform spherule suspension in the centrifuge tube was poured into the bottom of a 1000 ml Erlenmeyer flask containing 25 ml of 4 percent glucose and 40 mM lysine in water. With the container kept at 37 C. in a shaking water bath, a stream of nitrogen gas at 7 L/minute was flushed through the flask to slowly evaporate chloroform over 20 minutes. The liposomes were then isolated by 4-fold dilution of the suspension with normal saline and centrifugation of the suspension at 600×g for 5 minutes; the supernatant was decanted, and the liposome pellet was resuspended in 50 ml of normal saline. The liposomes were isolated again by centrifugation at 600×g for 5 minutes. The supernatant was again decanted and the pellet was resuspended in normal saline.

The foregoing description of the invention is exemplary for purposes of illustration and explanation. It should be understood that various modifications can be made without departing from the spirit and scope of the invention. Accordingly, the following claims are intended to be interpreted to embrace all such modifications.

TABLE 1

Pharmacokinetic parameters following 250-μg epidural injection

|  | DTC401 | MS |
|---|---|---|
| Cmax (ng/ml), CSF | 1960 ± 1280 | 6060 ± 3590 |
| Cmax (ng/ml), Serum | 86 ± 20 | 1460 ± 97 |
| t½ α (hr), CSF | 5.0 | 0.85 |
| t½ β (hr), CSF | 82 | 2.6 |
| t½ α (days), Serum | 0.48 | 0.68 |
| t½ β (hr), Serum | 49 | 5.0 |
| AUC (ng * days * ml$^{-1}$) CSF | 1170 | 432 |
| AUC (ng * days * ml$^{-1}$) Serum | 53 | 58 |

MS, morphine sulfate; Cmax, maximum concentration; t½ α, initial half-life; t½ β, terminal half-life; AUC, area under the curve.

What is claimed is:

1. A method for epidural administration to a vertebrate of a therapeutic compound comprising encapsulating a therapeutic compound in a drug delivery system having a sustained release rate of the compound from about 2 to about 7 days, and introducing the drug delivery system in a single epidural dose to the vertebrate, wherein the drug delivery system comprises multivesicular liposomes produced from the group consisting of egg phosphatidylcholines, dipalmitoylphosphatidylcholines, distearoylphosphatidylcholines, dioleoylphosphatidylcholines, dipalmitoylphosphatidylglycerols, dioleoylphosphatidylglycerols, and suitable combinations thereof.

2. The method of claim 1 wherein the multivesicular liposomes further comprise at least one steroid.

* * * * *